United States Patent [19]

Krabacher et al.

[11] Patent Number: 4,624,235
[45] Date of Patent: Nov. 25, 1986

[54] FORCE-TRIGGERED APPLANATION TONOMETER

[75] Inventors: Albert C. Krabacher, Lakewood, Colo.; George J. Eilers, 31537 Broadmoor Dr., Evergreen, Colo. 80439

[73] Assignee: George J. Eilers, Evergreen, Colo.

[21] Appl. No.: 599,967

[22] Filed: Apr. 13, 1984

[51] Int. Cl.$^4$ ............................................ A61B 3/16
[52] U.S. Cl. .................................................. 128/652
[58] Field of Search ............... 128/652, 645, 748, 774

[56] References Cited

U.S. PATENT DOCUMENTS 3,070,997 1/1963 Papritz et al. .................... 128/652
3,338,089 8/1967 Coombs, Jr. et al. ............. 128/652

FOREIGN PATENT DOCUMENTS 0157455 7/1961 U.S.S.R. ............................ 128/645

OTHER PUBLICATIONS

"Fast Automobile Ocular Pressure . . . ", Mackay et al., 6-7-60.

Primary Examiner—Edward Coven
Attorney, Agent, or Firm—Edward H. Berkowitz

[57] ABSTRACT

A portion of the cornea or similar flexible membrane is flattened by urging against the cornea a footplate with a measurable force and deriving a signal proportional to the magnitude of the applanated area of the cornea when the applanating force is compared to a threshold which corresponds to a force equal to a selected reference force on the planar footplate contacting the cornea. When the selected reference force signal is reached the area of the applanated region of the cornea is transferred as a signal for scaling by another signal proportional to the force.

9 Claims, 9 Drawing Figures

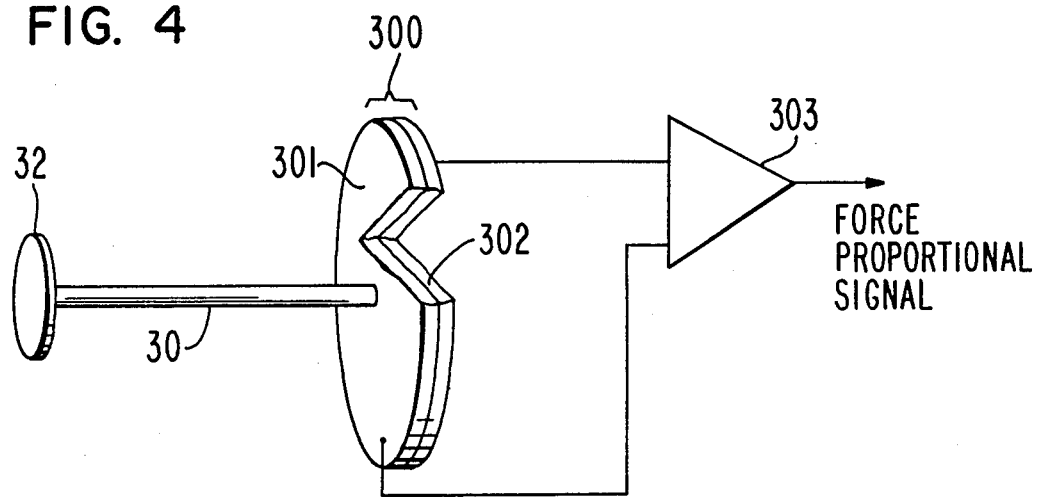
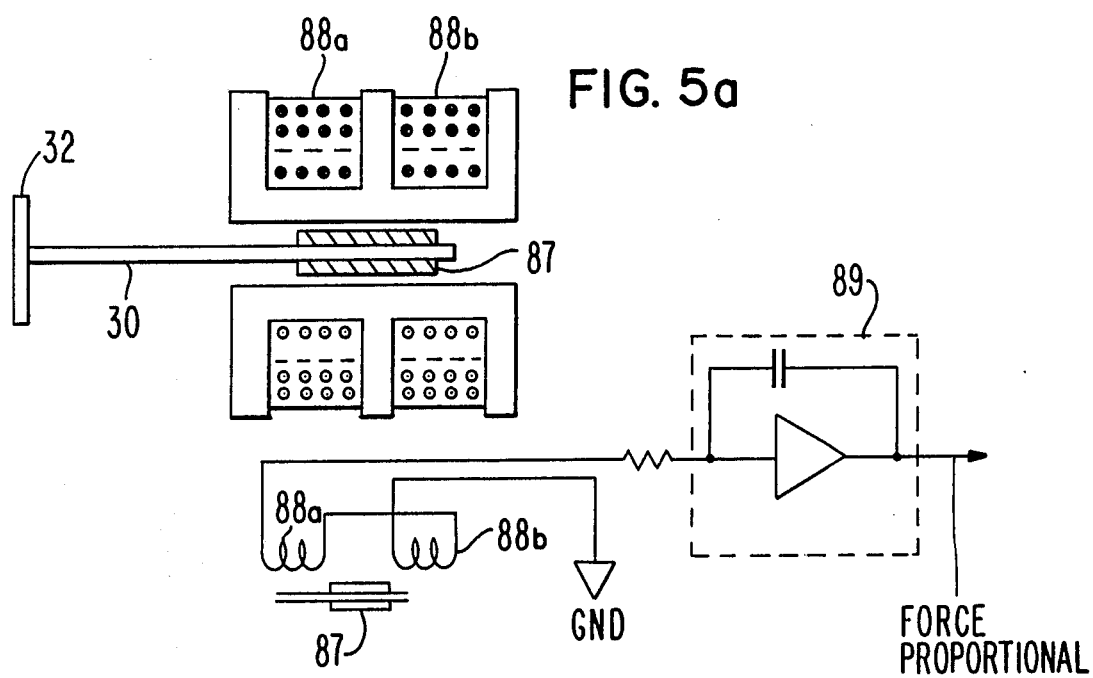

4,624,235

FORCE-TRIGGERED APPLANATION TONOMETER

FIELD OF THE INVENTION

The invention is in the field of tonometry and particularly relates to automated apparatus for opthamalogical measurements suitable for use without anaesthetic.

CROSS-REFERENCE TO RELATED APPLICATION

Copending U.S. Ser. No. 599,968, commonly filed herewith, describes other related inventions closely related to the present invention.

BACKGROUND OF THE INVENTION

The measurement of the intraocular hydrostatic pressure is a major diagnostic tool for the identification of eye disorders, especially glaucoma, and as such, apparatus capable of accurate and reliable measurement is greatly to be desired. Tonometry is used routinely for screening the population at large as well as following individuals with known pathology: consequently, risk, inconvenience and trauma must be minimized. Moreover, of those tested, the overwhelming majority will not exhibit intraocular pressure pathology. An accurate and reliable measurement is essential to assure that the screening does indeed identify incidence of abnormal intraocular pressure while not burdening the health care system with erroneous positive identification of pathology in normal individuals. Other desiderata include safety, non-invasiveness and practice of the method without the necessity of topical anaesthetic.

In the prior art, the Goldman tonometer has been a standard for opthamalogical measurement for many years. In this approach the intraocular pressure is obtained by flattening a standard area of the cornea to conform to a planar surface placed in contact with the cornea. Applanation tonometry, as the method is known, employs a circular transparent plane surface of precisely known diameter which is urged against the anaesthetized cornea while the observer confirms the applanation condition by observing the cornea through the transparent plane surface or footplate with the aid of a small amount of flourescein in the lacrimal fluid and a slit lamp or smilar light source. The optical source is preferably rich in the blue portion of the spectrum to excite the fluorescein and thereby provide enhanced contrast. The observer adjusts the pressure applied to the foot plate until the cornea just conforms to a circular region marked on the transparent foot plate, at which point the force urging the foot plate against the cornea is recorded.

Measurements of this type suffer from error in establishing the applanation condition. This determination is subjective and prone to error arising from, among other effects, the presence of a meniscus of tear fluid at the periphery of the foot plate and the resistance of the cornea to bending. A significant source of error and difficulty arises with the length of time required to adjust the device and to observe the flattened area. This may require an interval ranging from a few seconds to a minute or more. It is difficult for the subject to maintain the eye in a fixed position for that period without blinking. Moreover, such protracted contact of the instrument with the cornea increases the risk of a scratch or other trauma because of the prolonged contact and the possiblity of gross eye movements. Clearly, the prolonged contact also requires application of an anaesthetic to the eye.

A significant improvement in applanation tonometry apparatus due to Mackay and Marg (see Marg et al, Archiv. Opthalm., v.4, no.1, pp 67–74 (1961) and references therein) utilizes electronic means to measure the force required to produce the applanation condition between the foot plate and the cornea, deriving a signal proportional to the applied force. The force is necessarily applied as a function of time and the resulting displacement of a plunger linking the cornea with the central region of the foot plate is monitored on a trace recorder. In the Mackay-Marg instrument the trace characteristically rises to a first relative maximum as the central plunger responds to the full corneal resistance and the intraocular pressure. As the cornea is applanated against the footplate region surrounding the central plunger, the corneal resistance is distributed over the annular region and the signal derived from the plunger displacement drops to a relative minimum, thereafter rising monotonically as the cornea continues to yield in response to the increasing pressure. A second maximum will be recorded when the area of the cornea applanated by the probe reaches its maximum. As the probe is withdrawn, the sequence is reversed and a near mirror image of the trace is generated. For this type instrument it has been found that the significant indicia for establishing the magnitude of the intraocular pressure is the relative amplitude of the aforementioned relative minimum or trough with respect to the baseline of the trace. The force measurement is derived from the displacement of the plunger. The displacement is quite small, of the order of a micron. The Mackay-Marg tonometer is (at least in principle) free of the need for an anaesthetic because the entire measurement is obtained in an interval of the order of 10's of milliseconds. An interpretation of the complex trace is still required for this instrument to extract the critical intraocular pressure parameter.

BRIEF SUMMARY OF THE INVENTION

It is an object of the invention to provide an improved tonometer especially exhibiting improved consistency in measurement.

It is another object to simplify tonometrical instrumentation and to reduce the influence of subjective judgement in both acquisition and interpretation of the data.

In one feature of the invention a selected force is applied to a planar probe in contact with the cornea.

In another feature of the invention means are provided to electronically monitor the magnitude of the applanation area.

In yet another feature of the invention comparator means are provided to trigger the measurement of the instantaneous applanation area upon sensing equality to, or an excess thereof over a selected threshold value of the applanation force.

In still yet another feature of the invention scaling means are provided to compute and display the pressure obtained from the measured area.

In again another feature of the invention, the applanation area is continuously sensed by measurement of the capacitive reactance from the planar probe to ground potential as referenced from the cornea.

In one simple embodiment a linear variable differential transformer (LVDT) is disposed to sense the applied force through the force-displacement relationship of the springs which support a shaft coupling the LVDT to the footplate of the instrument. Such devices are well known and have been employed in similar fashion in the art. The foot plate of the tonometer transmits the applied force through the shaft from the cornea to the armature of the LVDT. The force sensed from the output fo the LVDT (or other alternative device for obtaining a force proportional signal) is compared with a reference in a comparator and when equality with the reference is sensed a trigger signal is generated. An insulative sheet of known dielectric constant and geometry provides D.C. isolation between the cornea and the foot plate to which an A.C. signal is applied. The A.C. current to ground (the cornea) is measured to ascertain the capacity which in turn is determined by the applanation area. Upon the triggering signal from the force signal comparator, the A.C. current for a constant voltage (or the A.C. voltage for constant current) is sampled and presented to an amplifier to yield an area proportional signal.

The foregoing objectives, features and advantages of the present invention will appear from the following more particular description as illustrated in the accompanying drawings.

BRIEF DESCRIPTIONS OF THE DRAWINGS

FIG. 4 represents a piezo-electric transducer for the footplate of the present invention.

FIG. 5a shows another embodiment for a variable reluctance force proportional transducer, and FIG. 5b illustrates the basic circuit therefore.

DETAILED DESCRIPTION OF THE INVENTION

Figure 1A:
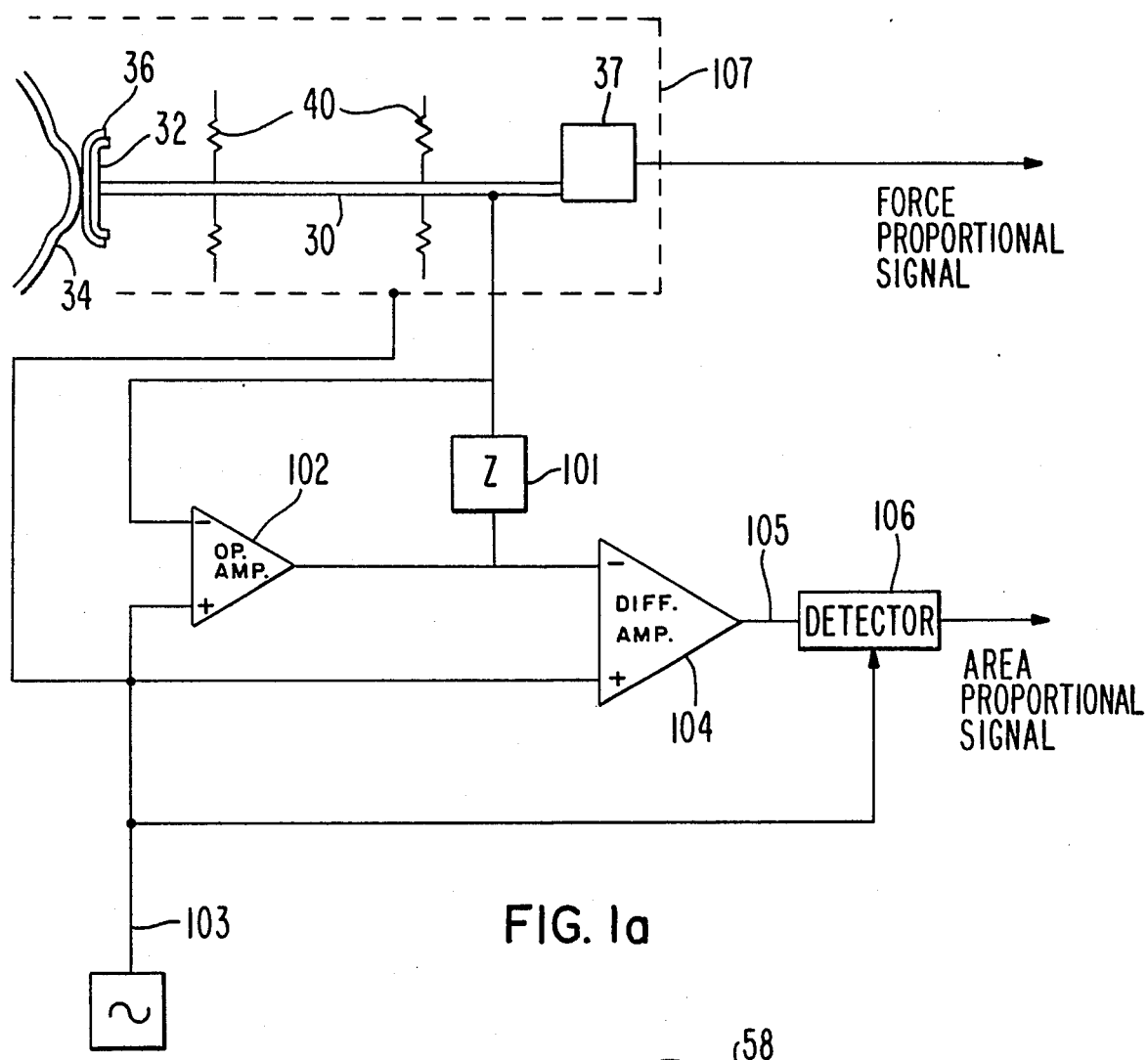
FIG. 1a is a schematic explanation of an embodiment of the present invention.

One simple embodiment is shown schematically in FIG. 1. A shaft 30 supports a foot plate 32 which bears against the cornear 34 for an internal pressure measurement. The foot plate is electrically isolated from cornea 34 by dielectric 36 and the shaft is isolated from ground by appropriate means. The force exerted by the cornea against the foot plate is balanced by springs 40. The relative displacement of the shaft 30 is ascertainable by means of a linear displacement sensor 37 from which a signal is taken and which is calibrated to yield a force proportional signal in accord with $$F = -kx$$

where k is the spring constant for the springs 40 and x is the relative displacement of the shaft 30.

An AC signal 103 is presented to a high gain operational amplifier 102 which is connected in such manner that the signal applied to footplate 32 exaclty duplicates the AC signal 103. The voltage appearing on the footplate is returned to the inverting input 202 of the operational amplifier 102. A difference appearing between the excitation signal 103 and the footplate signal will be greatly amplified and will appear at the output. The amplified output is, in turn, connected to the footplate through series impedance 101 of magnitude Z. Provided that certain stability requirements are met and that the gain of operational amplifier 102 is sufficiently large (of the order of $10^3$ to $10^5$), the footplate potential will be a very close reproduction of the excitation signal 103. Any current flowing from the operational amaplifier output to footplate 32 will necessarily flow through series impedance 101 thereby imposing a potential difference between the inputs of the differential amplifier 104. The voltage difference will be proportional to the current flowing to the footplate 32 and proportional to the impedance Z.

The footplate 32, shaft 30, springs 40, and associated items electrically connected to the footplate are guarded by a shield 107 driven to the same potential as the footplate. Current flowing into the footplate results from the capacitive coupling to the cornea. The capicitive coupling is clearly proportional to the contact area between the cornea and the footplate. The surface of the cornea is relatively good conductor and is maintained at ground potential through the electrical contact of the patient with his environment or by the relatively large capacitive to ground presented by the human body even without direct ohmic contact to ground. If the impendance 101 is capacitative, the voltage developed a cross it will be in phase with the excitation 103 because the footplate current will lead the phase of excitation signal 103 by 90°. This current will in turn produce a drop across the capacitor that lags the phase of the current by 90°, thereby producing a resulting voltage signal at the differential amplifier that is in phase with the excitation signal 103. It is apparent that the impedance 101 need not be a capacitative reactance: it is only necessary to note that the voltage developed across it and the phase relationship for that voltage are selectable by the designer. The detector 106 is preferably a phase sensitive circuit in order to exploit synchronous properties and enhance noise rejection. It is important to note that phase sensitive detector is not essential for this application and a peak detector, envelope detector or similar means for producing a dc signal from the ac signal across impedance 101 would be suitable (although somewhat less satisfactory) for the purpose.

Figure 1B:
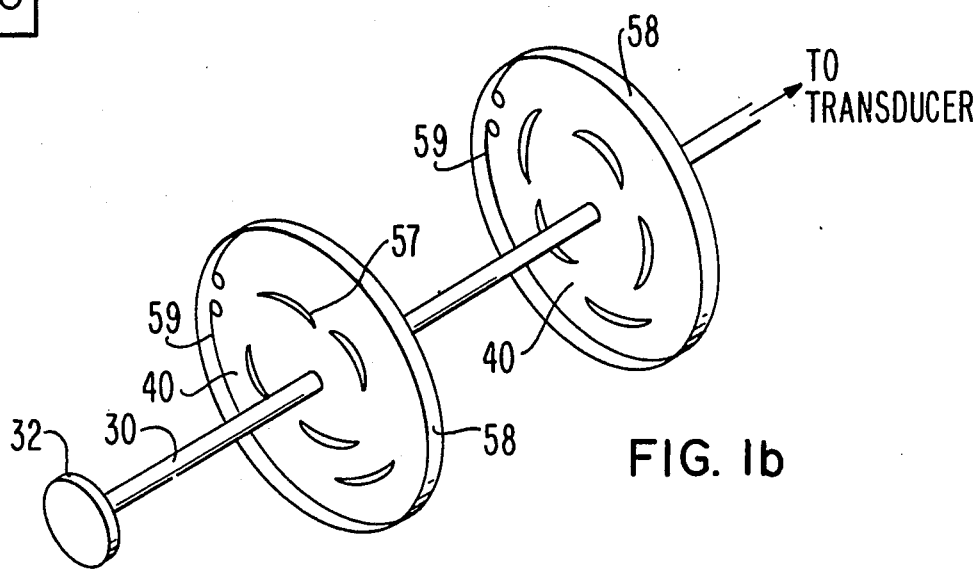
FIG. 1b is a schematic representation of a mechanical suspension.

One suitable mechanical suspension for support of shaft 30 is illustrated in FIG. 1b which is a schematic perspective illustration of a flat spring suspension structure. Flat springs 40 are formed by etching a metal foil. Arc segment perforations, as shown are found to provide enhanced radial compliance and a wide dynamic range. Spring carriers 58 are secured to probe housing 107 and the springs 40 are held in the respective carrier, against the end plate thereof by a metal ring 59 press fit into the carrier ends.

An A.C. signal of constant amplitude is applied to shaft 30 and a high input impedance amplifier receives the signal to ground through the capacitive impedance presented by dielectric 36. The signal from the impedance divider is proportional to the impedance presented by the capacitive coupling to the cornea.

In operation the force proportional signal is adjusted to a selected reference value through a comparator and a trigger signal is derived whenever the force proportional signal equals the selected value presented as reference input to the comparator.

The response of the present apparatus is noted to produce signals which are monotonic functions of applanation in contrast to the complex signal obtained from the prior art instrument of Mackay and Marg.

It is recognized in the field of tonometry that the cornea is not perfectly flexible and the finite rigidity of the cornea provides an apparent increment to the measured pressure. It is also known that surface tension forces operate between the lacrimal fluid and the exterior corneal surface to reduce the applied force required for a given deformation. These two effects are oppositely directed and it has been determined that for the standard applanated areaof prior art (3.06 mm diameter) the two effects are of approximately equal magnitude: thus, for this standard area, the pressure derived from independent area and force sensors need not be corrected for these two effects (within the accuracy of their cancellation). In copending U.S. Ser. No. 599,968, a standard area is directly selectable through a proportional signal for operation directly comparable with prior art, if so desired. The present invention describes an instrument properly regarded as referencing measurements to a standard applanating force.

As above described, one embodiment of the subject tonometer monitors one parameter (area) in a substantially continuous manner and for a critical preselected magnitude of the applanation area there is developed a trigger signal for obtaining a signal proportional to the applied force. It is recognized that the response of the cornea or other deformable membrane to the applanation may be continuously monitored in both the area signal and the force signal to establish the continuous, two-dimensional response function rather than a particular discrete point on that function. One thereby obtains access to a wealth of information latent in the shape of the response function. Corneal rigidity, hysteresis, corneal bending and like quantifiable parameters are thereby accessible to measurement and study. It is noted that the choice of foot plate area was selected in the prior art to substantially minimize a corneal rigidity effect. One may well wish to measure the effect of corneal rigidity and other attributes which may contribute to effective diagnoses. The localization of regions of this generalized two-dimensional function space for study is accomplished in straightforward fashion by constraint of signals or by constraints imposed upon the recorded two-dimensional data.

Figure 2:
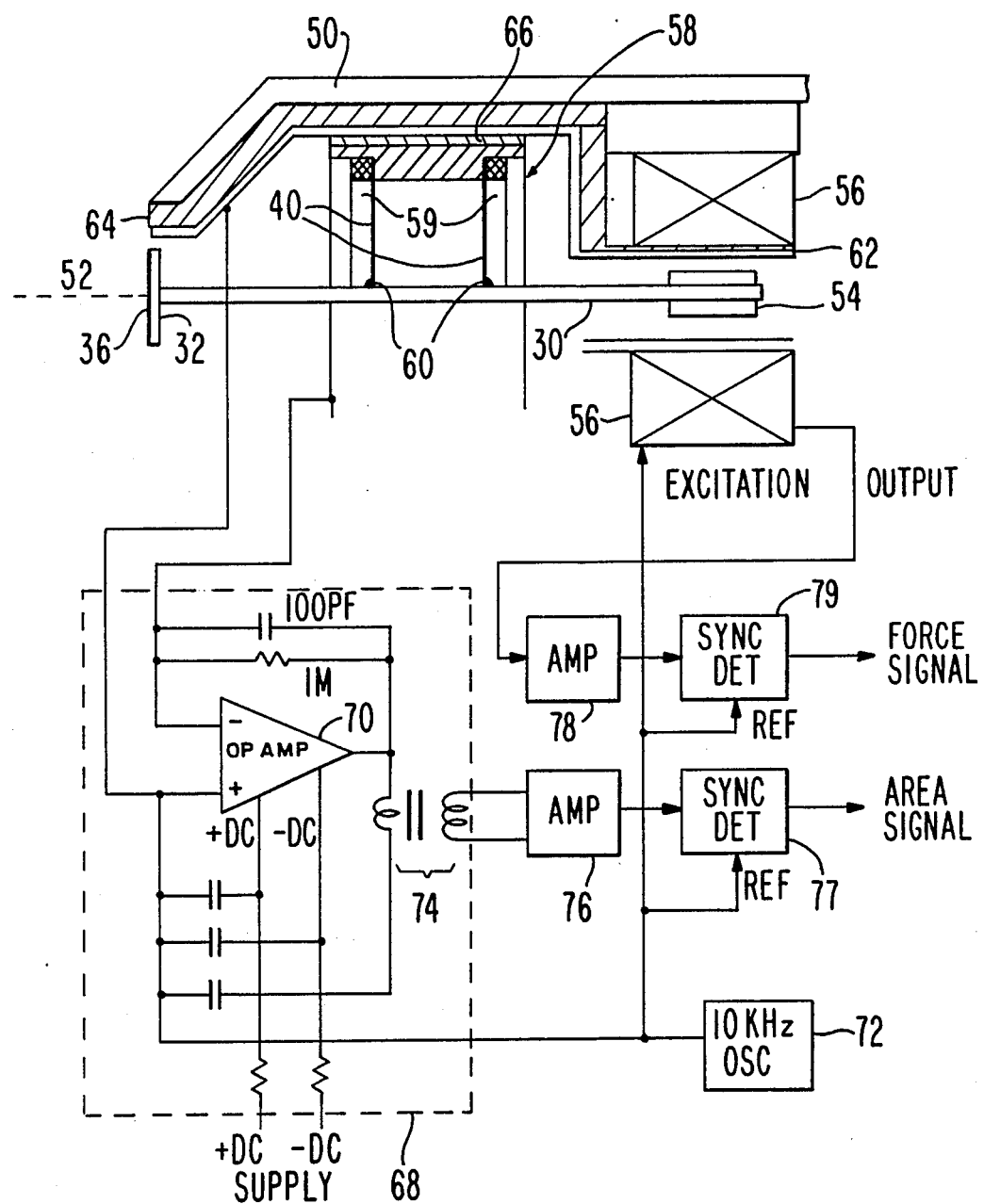
FIG. 2a is a partial section of a a probe assembly and associated basic signal processing.
FIG. 2b is an alternate electrical connection structure for the footplate signal.

A more detailed exposition of a preferred clinical embodiment with reference to corneal tonometry is shown in FIG. 2a. A probe case 50 of cylindrical symmetry contains LVDT windings 56 which effectuate sensing the displacement of the LVDT core 54. The LVDT comprises three windings: a driven primary and two symmetrically situated secondaries, connected in series opposed form. The flux arising from the driven primary links the core and the two secondaries. With the core 54 at zero displacement, symmetrically disposed with respect to the secondaries, equal opposed voltages are induced across the secondaries for a net null signal. Upon displacement of the core 54, the voltages across the secondaries become unbalanced and a difference signal obtained from the LVDT exhibits phase and amplitude dependent upon the direction and magnitude of the displacement. This signal is then processed to yield a waveform faithfully reproducing the motion of the core.

The LVDT core 54 is supported near one end of shaft 30 with foot plate 32 at the other end. Hypodermic syringe stock is recommened as an excellent available stock for shaft construction. A thin insulating film constitutes the dielectric of a capacitive coupling between foot plate 32 and the cornea. The insulating film 36 may be a polymeric coating, a glass or fused silicon dioxide. Polyurethane, mylar, polyethylene, polyester, epoxy, acrylic and the like are all very good examples for this purpose because these substances exhibit relatively low toxicicity and because they exhibit high dielectric constants. Glass or silicon dioxide films have the advantage of superior chemical and dimensional stability as well as damage resistance owing to their hardness. Certain other materials, such as anodized aluminum, are also suitable.

Figure 2B:
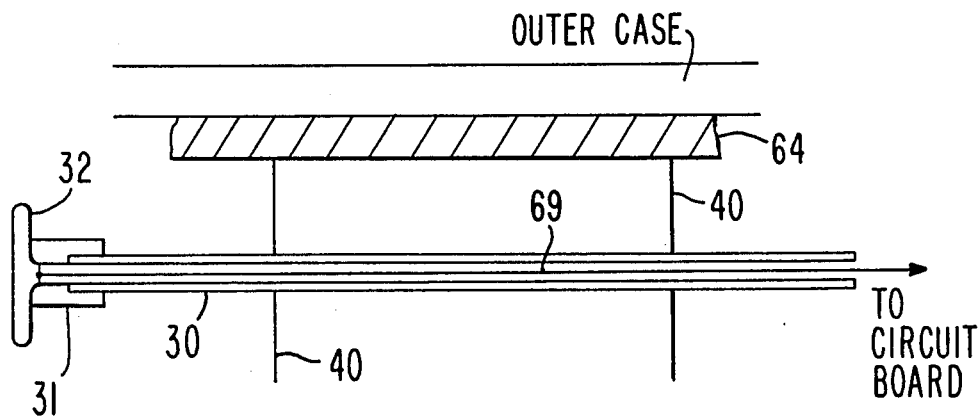

A spring carrier 58 is mechanicaly secured to the probe case 50 to support the shaft 30 via support springs 40 and to provide electrical coupling thereto. An apprpriate spring suspension which has been employed for this application is shown in FIG. 2b wherein a metal foil is etched to remove annular segments as shown in FIG. 1b. The resulting flat springs are secured to the spring carrier by a press fit ring. The shaft 30 is secured to the central hole by bonds 60 formed from known conducting epoxy resin.

Capactive coupling to the cornea through foot plate 32 and dielectric film 36 results in an area proportional signal if spurious currents through stray capacitances can be eliminated or compensated. For this purpose, the probe structure incorporates a guard conductor shell 62 surrounding the foot plate 32, shaft 30 and spring suspension. Insulating shell 64 isolates the guard conductor 62 from the probe case 50 and insulator 66 likewise isolates the spring carrier 58 from guard conductor 62.

A preamplifier 68 preferably housed inside of guard conductor 62 comprises a differential ampifier 70 for comparison of the foot plate signal separately from the parasitic currents arising from the stray capacitances.

A preferred structural variation of the above described probe is shown in FIG. 2b. The footplate 32 is here joined mechanically to hollow shaft 30 through insulated collar 31. An electrical coupling from footplate 32 to preamplifier 70 is realized from an insulated conductor 69 which is carried coaxially in hollow shaft 30. The springs 40 are alos electrically isolated from the shaft 30 and the later is, in this variation, driven to guard potential.

It is useful at this point to consider the amplitude of the desired capacitive current resulting from contact between the cornea and foot plate 36. Consider a representative thickness of 0.001 inch (25.4 microns) and a relative dielectric constant of 3.6 for the dielectric film 36. Glasses, and in particular fused silicon dioxide exhibit dielectric constants in this range and many common polymeric coatings have similar dielectric constants.

Oscillator 72 provides an AC excitation at a frequency which for present purposes can be assmed as 10 KHz. Under the assumption of a 10 volt peak signal the AC current through the foot plate 32 is very nearly 6 microamperes. While this is not difficult to measure directly, the effects of parasitic capacitance (which can induce currents that reach or exceed this value) are effectively removed by floating the guard shell conductor and the entire preamplifier to foot plate potential. The signal is amplified to the point where interwinding capacitance introduces neligible effects, at which point the signal is returned to ground through transformer coupling 74. This area proportional signal is again amplified by linear amplifier 76, phase detected against the oscillator reference signal in sync detector 77 from which there is obtained a DC signal representative of the applanation area. In the same fashion, the LVDT excitation is amplified by amplifier 78 and phase detected against the oscillator reference at sync detector 79 to yield a force proportional DC signal.

Figure 3:
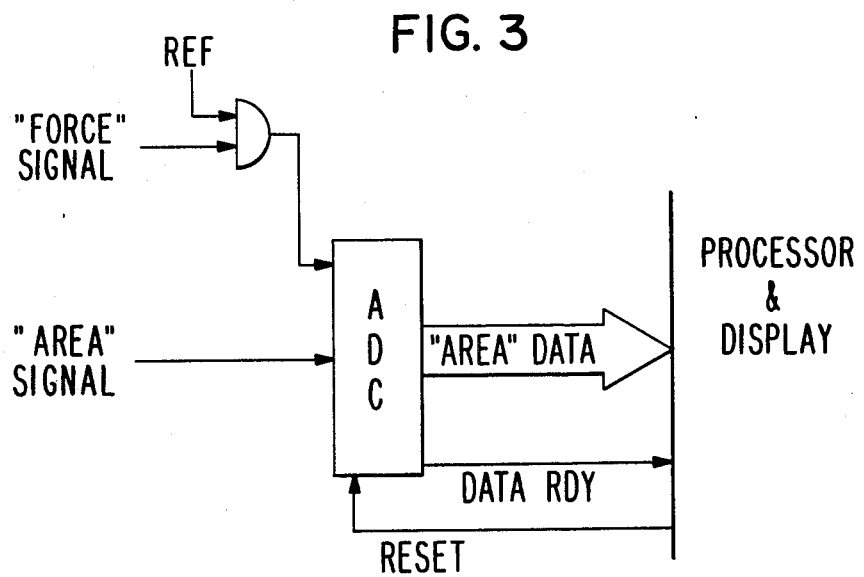
FIG. 3 is a symbolic diagram of another type of signal processing.

A more specialized apparatus may be obtained following FIG. 3 wherein the force proportional signal is compared with a reference level to gate an area proportional datum to a processor to yield a pressure variable for display. A preferred addition to this arrangement is an electrical contact means responsive to the motion of the shaft 30, in turn dependent upon the applanating force. In this manner threshold sensing triggered from a reference magnitude force would be acheived in a particularly simple manner.

It is noted that further processing of the measured proportional signal, if desired, is symbolically contained within a logic unit (not shown). An example of such optional processing would be an averaged sampling of the sensor transient on both the rising and falling sides, corresponding to rise and fall of the applanation condition. (There are technical reasons which tend to reduce the value of sampling on the falling portion of the transient for simple intraocular pressure measurement.) The logic unit processes the signal in accordance with the relationship of the derived parameter (intraocular pressure, for example) to the force response transient, which in the present apparatus contrasts with the transient waveform of the McKay-Marg instrument. The work of Mackay and Marg suggest that the intraocular pressure is proportional to the amplitude of the relative minimum of the transient force response waveform. The operational principle underlying the transient waveform of the present apparatus yields a monotonic function, which when scaled at a selected area magnitude accurately measures the intra-ocular pressure. Further optional processing, already alluded to herein, includes multiple sampling at known succesive values of the area proportional signal to yield a two parameter analysis of the corneal behaviour. The details of this aspect of the processing are outside the scope of the present invention.

One will readily appreciate that alternative pressure sensing means can be employed in the form of a piezoelectric transducer for direct sensing of the applied force. A piezoelectric transducer is conceptually illustrated in FIG. 4 wherein a footplate 32 is supported as in other embodiments by shaft 30. The distal end of shaft 30 is bonded to a bimorph piezoelectric element 300. The latter typically comprises a conductor such as an aluminum disk 301 bonded to a peizoelectric crystal 302. The force applied to the footplate in contact with the cornea is transmitted through shaft 30 to the bimorph disk 300 causing the latter to assume a slightly concave shape, thereby inducing radial tensile stresses in the peizo crystal. A potential developed between the plane surfaces of the bimorph sensor 300 is proportional to the transient applied force and the resulting voltage pulse is directed to a high impedance amplifier 303. A pulse with amplitude proportional to the applied force is thereby obtained for use in processing as in the above described embodiments.

Another transducer for obtaining a force proportional signal is illustrated in FIGS. 5a and 5b. This variable reluctance sensor is structuraly similar to the LVDT with the distinction that no AC excitation, AC amplifier nor synchronous detection are employed. As distinct from the LVDT apparatus, which develops a signal proportional to the absolute displacement of the LVDT core, the variable reluctance sensor yields a signal proportional to dz/dt, the rate of displacement along the z axis of a permanent magnet 87 with respect to windings 88a and 88b. In principle this signal can be integrated by integrator 89 to yield the z displacement. Sufficient integration is inherent in an AC amplifier exhibiting aapproximately −20 db/decade rolloff over the appropriate frequency range (about 1 to 100 Hz). The resulting pulse amplitude is therefore force proportional through the displacement proportionality and may be treated as in the above embodiments.

Figure 6:
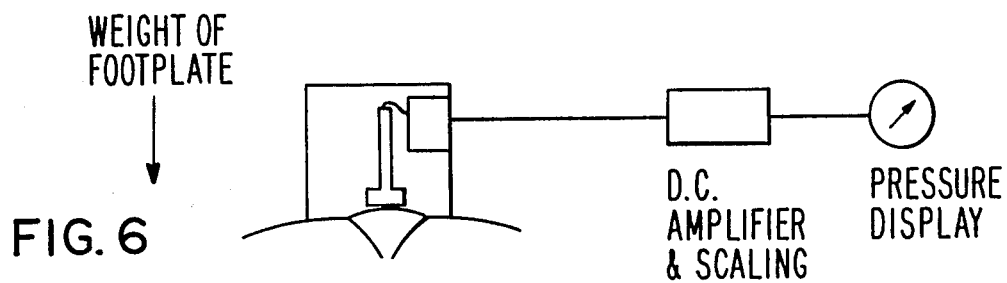
FIG. 6 shows a constant applanation force-referenced tonometer.

In the above described embodiments, electrical measurements of the applanated area proportional signal and applanation force proportional signal are combined to yield the desired pressure proportional signal. Another approach, further described in the aforesaid copending U.S. Ser. No. 599,968, utilizes an area proportional signal as before, but the probe now comprises a structure supported directly on the cornea of a supine patient, as schematically illustrated in FIG. 6. The applanation of the cornea under gravity against the footplate 32 defines a standard reference value (which is not, as in the present invention, simply adjusted by varying a reference level input to a comparator) and it is only necessary to measure the resulting area proportional signal as discussed herein to obtain a signal which transforms to a pressure indicia. It is recognized that both the constant (reference) force and the force triggered tonometer (the present invention) differ from standard practice in tonometry in the precise prinicple of a fixed applanating force and variable degree of applanation whereas standard practice as well as above described embodiments emphasize a fixed reference applanation area and variable applanation force.

It will be apparent that many changes could be made in the above method and apparatus and many apparently different embodiments of this invention could be made without departing from the scope thereof; it is therefore intended that all matter contained in the above description and shown in the accompanying drawings shall be interpreted as illustrative and not in a limiting sense.

What is claimed is:

1. An applanation tonometer for ascertaining the internal hydrostatic pressure of a flexible body containing a fluid, said body subject to curvature due to said internal hydrostatic pressure, comprising
   (a) a footplate comprising a planar portion for bearing against said flexible body, a shaft for supporting said footplate and a guard electrode spaced apart from said footplate and substantially surrounding said footplate,
   (b) housing means for supporting said footplate in a housing, said housing means capable of displacement toward said body whereby a portion of the surface of said flexible body is flattened against against said footplate,
   (c) force sensing means for ascertaining the magnitude of the force exerted by said body against said footplate and for generating a force proportional signal,
   (d) area signal generating means for developing a signal proportional to the area of said flexible body in contact with said footplate comprising oscilator means for driving both said footplate and said guard electrode to the same a.c. potential, (e) comparator means responsive to said force proportional signal means for establishing the equality or excess of said force proportional signal with respect to a threshold value of selectable magnitude for generating a trigger signal, (f) scaling means responsive to said trigger signal for operating on the instantaneous signal magnitude of said area proportional signal with a quantity dependent upon said force proportional signal to obtain a pressure value, and (g) display means to indicate said pressure value.

2. The applanation tonometer of claim 1 wherein said housing means further comprises spring means for coupling said shaft to said housing means.

3. The applanation tonometer of claim 2 wherein said area signal generating means comprises means for measuring the capacitive reactance of said footplate in series with said flexible body.

4. The applanation tonometer of claim 2 wherein said force sensing means comprises a linear variable differential transformer mechanically coupled to said shaft.

5. The applanation tonometer of claim 2 wherein said force sensing means comprises a piezo electric transducer mechanically coupled to said shaft.

6. The applanation tonometer of claim 2 wherein said force sensing means comprises variable reluctance transducer means to generate a signal responsive to the displacement of said footplate.

7. The method of measuring the internal hydrostatic pressure within a flexible body containing a fluid, said body bounded by walls, said walls outwardly curved due to said hydrostatic pressure, comprising the steps of (a) applying a force against a portion of said outwardly curved walls to deform a portion thereof to conform to a planar surface portion, (b) sensing the area of said planar portion of the surface of said flexible body, comprising the steps of coupling an oscillatory current through said planar aspect of the deformed body while maintaining an equipotential surface substantially about said oscillatory current in the neighborhood of said planar aspect by applying an oscilating potential to said surface, said oscillating potential corresponding to said oscillatory current in phase and substantially equal to the potential at said planar aspect, (c) generating a trigger signal upon detecting a preselected relative magnitude of said force proportional signal with a selected value, (d) measuring the magnitude of said area applanated upon the detecting of said preselected relative magnitude, (e) computing the ratio of said applied force to said area, and (f) displaying said ratio.

8. In corneal applanation tonometer, (a) footplate means for applanating the subject cornea, comprising an applanating disk having a dielectric layer disposed on one side thereof, and footplate support means for supporting said footplate means in contact with the cornea whereby a portion of said cornea is flattened against said footplate means, (b) guard electrode means substantially surrounding said footplate means and spaced apart therefrom for providing a controlled equipotential surface thereabout, (c) oscillator means providing an oscillating current coupled to said guard electrode means through a first impedance and coupled to said footplate means through a second impedance and thence through said dielectric layer to the cornea, (d) differential amplifier means having respective inputs coupled to said footplate means and said guard electrode means for obtaining a difference signal proportional to the oscillating potential difference between said footplate means and said guard electrode means, (e) phase sensitive detector means for developing a d.c. signal from the phase related difference signal and oscillator means, whereby said d.c. signal represents the capacitive impedance coupling of said corneal and said footplate means and thus said d.c. signal comprising an area proportional signal dependent upon said flattened area of said cornea, and (f) force sensing means for obtaining a force proportional signal depending in magnitude upon the force applied by the cornea against said footplate means, (g) discriminator means for comparing said force proportional signal against a reference level and deriving therefrom a trigger signal for gating said area proportional signal.

9. The apparatus of claim 8 comprising display means for representing said gated area proportional signal.

* * * * *